United States Patent
Zucchi et al.

(10) Patent No.: US 8,187,523 B2
(45) Date of Patent: May 29, 2012

(54) METHOD FOR MANUFACTURING A CUFF ON PLASTIC TUBE PROVIDED WITH AN EXTERNAL SHEATH

(75) Inventors: Giuseppe Zucchi, S. Possidonio (IT); Daniele Resca, San Felice Sul Panaro (IT); Alessandra Pedarzini, Finale Emilia (IT)

(73) Assignee: Covidien AG, Neuhausen am Rheinfall (CH)

( * ) Notice: Subject to any disclaimer, the term of this patent is extended or adjusted under 35 U.S.C. 154(b) by 245 days.

(21) Appl. No.: 12/556,070

(22) Filed: Sep. 9, 2009

(65) Prior Publication Data
US 2010/0192956 A1 Aug. 5, 2010

(30) Foreign Application Priority Data
Feb. 5, 2009 (IT) .............................. BO2009A0055

(51) Int. Cl.
*B29D 24/00* (2006.01)

(52) U.S. Cl. ........ 264/516; 264/138; 264/259; 264/512; 156/156; 156/285; 156/287

(58) Field of Classification Search .................. 264/138, 264/259, 512, 516; 156/156, 285, 287
See application file for complete search history.

(56) References Cited

U.S. PATENT DOCUMENTS

| 4,411,055 | A | * | 10/1983 | Simpson et al. ................. 29/447 |
| 4,495,134 | A | * | 1/1985 | Ouchi et al. .................. 264/516 |
| 5,951,513 | A | * | 9/1999 | Miraki ........................ 604/96.01 |
| 6,599,462 | B1 | * | 7/2003 | Miraki ........................... 264/456 |
| 2002/0160134 | A1 | * | 10/2002 | Ogushi et al. ................ 428/35.7 |
| 2007/0006964 | A1 | * | 1/2007 | Lee ................................ 156/219 |

FOREIGN PATENT DOCUMENTS
WO WO 2007/102759 * 9/2007

OTHER PUBLICATIONS
Italian Search Report for Appln. No. IT BO20090055 completed Nov. 19, 2009.
European Search Report for European Appln. No. 09 01 0543 completed Jun. 21, 2010.

* cited by examiner

*Primary Examiner* — Christina Johnson
*Assistant Examiner* — Saeed Huda
(74) *Attorney, Agent, or Firm* — Carter, DeLuca, Farrell & Schmidt LLP

(57) ABSTRACT

Method for manufacturing a cuff on a plastic tube comprising an inner tube and an outer sheath covering said inner tube. The outer sheath comprises at least a portion to be molded for producing a cuff. The method comprises a covering step including an injection operation in which air is intermittently or continuously injected between the inner tube and sheath.

11 Claims, 3 Drawing Sheets

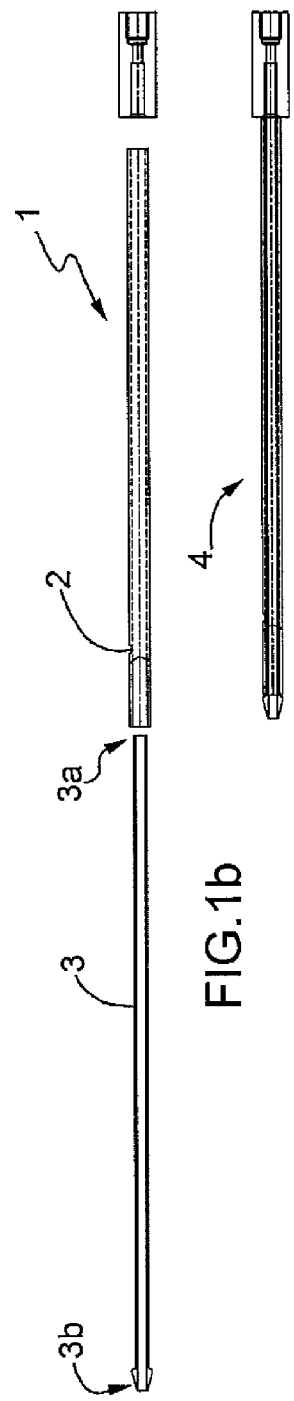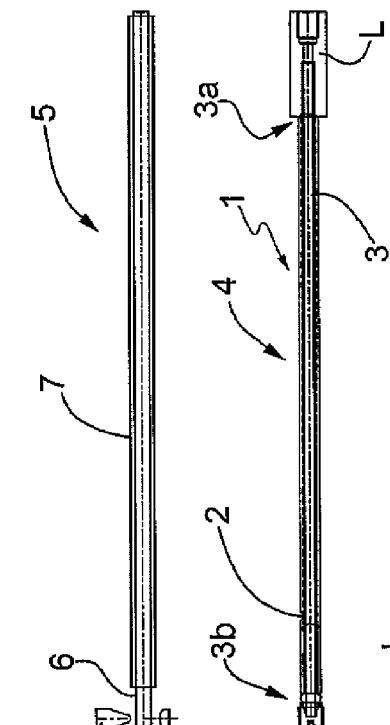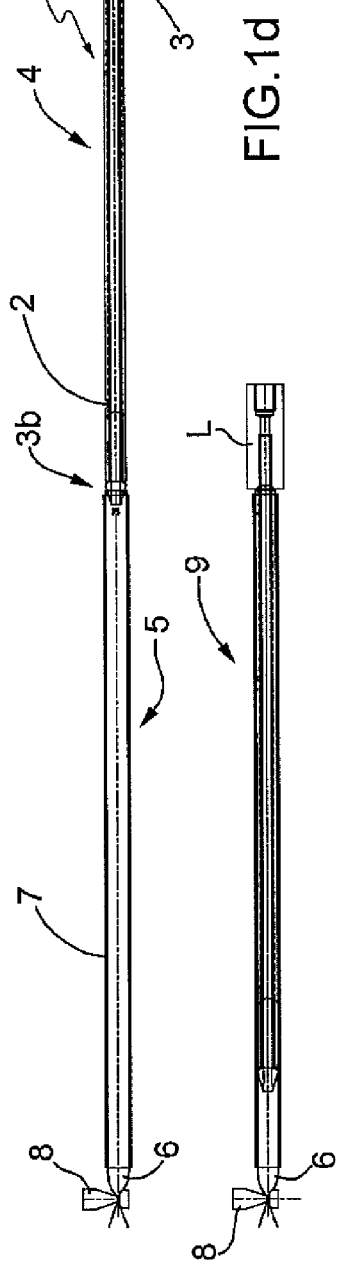
FIG.1a
FIG.1b
FIG.1c
FIG.1d

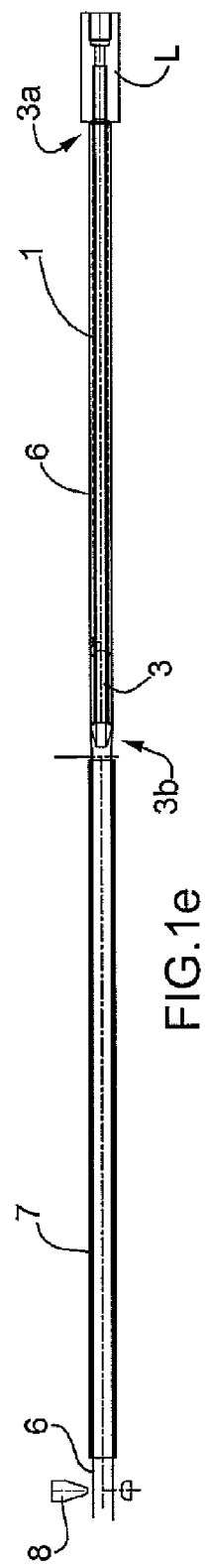
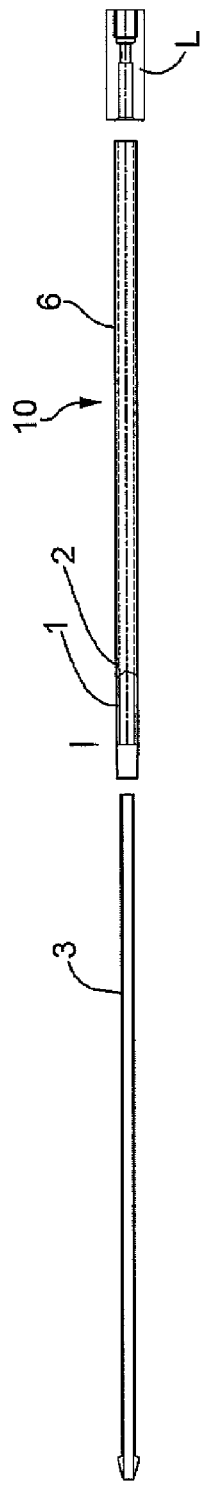
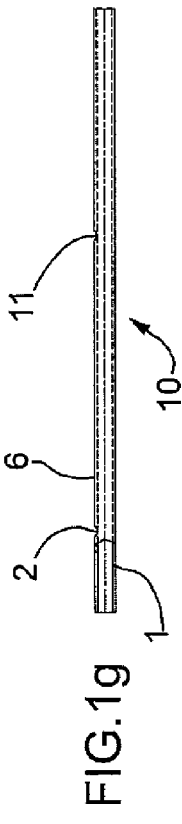
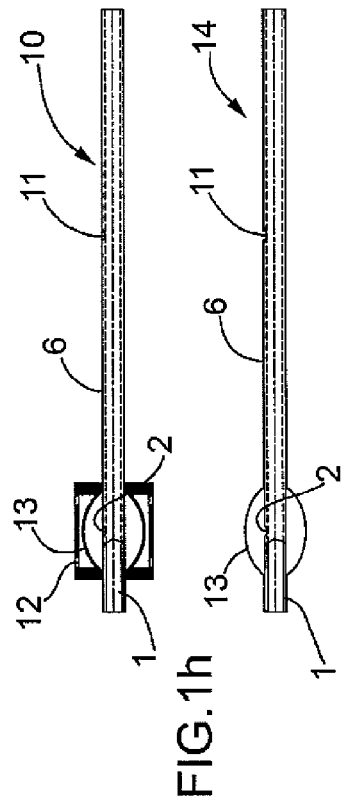
FIG.1e
FIG.1f
FIG.1g
FIG.1h

METHOD FOR MANUFACTURING A CUFF ON PLASTIC TUBE PROVIDED WITH AN EXTERNAL SHEATH

TECHNICAL FIELD

The present disclosure concerns a method for manufacturing a cuff on a plastic tube provided with an external sheath. In particular, the present disclosure is advantageously used in the manufacture of tracheal tubes or tracheostomy cannulas.

BACKGROUND

Here and hereinafter the term "cuff" is intended to mean an inflatable balloon attached around a tube, e.g. a tracheal tube. In tracheal tubes the purpose of the cuff is to function as a seal between the tube and the trachea, in order to prevent air from getting out and bacteria to enter the lungs. In other catheters, e.g. urine catheters, the purpose of the cuff is to block and secure the tube in the body part where it is inserted into.

Tracheal tubes are used as means of conveying air or gas mixtures delivered by an Intensive Care Unit or Anaesthesia ventilator, through a breathing circuit, into the patient airways. Tracheostomy cannulas can have the same use as tracheal tubes or are just installed on spontaneously breathing patients who for a particular disease or accidental reasons cannot breath autonomously and sufficiently without this airway bypass.

Usually, the cuff is obtained through a blowing process or an alternative technology of pre-extruded tubing expansion. The assembly process of the cuff on the tube consists of the following phases: cutting of the cuff ends, named collars; insertion of the so obtained cuff on the tube and correcting its positioning; and gluing with solvents or adhesive.

The result obtained from the above process is the formation of a kind of step next to the collar cutting edge. This step represents a traumatic factor during intubation operation because of the possible abrasions it can cause. This problem is particularly serious for children and infant patients where the diameter of the tubes is narrower and the collar thickness is crucial.

Another problem of the prior art process relates to manufacturing issues. In fact, the shaping and the assembly operations render the whole process slow, expensive and relying heavily on personnel experience and ability. It is important to notice that such problems become more relevant when the tube has a narrow diameter (e.g. for children and infant patients) and when the cuffs are made of polyurethane with reduced thickness and easy to be damaged during handling, tubing and gluing.

A way to overcome the above drawbacks is disclosed in for example, EP1733752A1, the entire contents of which is hereby incorporated by reference. This patent discloses a method to obtain a tube provided with an external sheath with which the cuff is formed. This method provides the adding of an anti-adherent agent in the zone of the cuff shaping. As it can be obvious for a person skilled in the art, the presence and the use of an anti-adherent agent can however involve a series of technical and economic inconveniences.

Accordingly, there is a need for manufacturing a cuff on plastic tubes provided with an external sheath whose technical characteristics are such to avoid the use of anti-adherent materials.

SUMMARY

A method for manufacturing a plastic tube having a cuff thereon is provided which includes comprising the steps of: covering an inner tube with an outer sheath, said outer sheath including at least a portion configured to be molded for producing a cuff; and injecting air between said inner tube and said sheath.

BRIEF DESCRIPTION OF THE DRAWINGS

Various embodiments of the present disclosure will be described herein below with reference to the figures wherein:

FIGS. 1a-1h illustrate the steps of a method for manufacturing a plastic tube provided with an external sheath in accordance with an embodiment of the present disclosure.

DETAILED DESCRIPTION

Figure 2A:
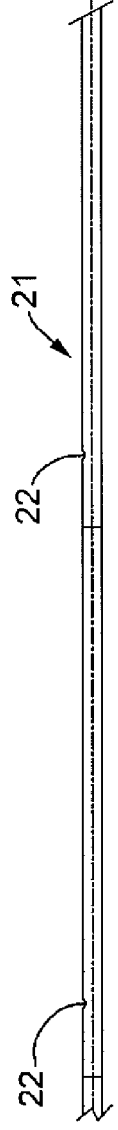
FIGS. 2a-2d describe the steps of a method for manufacturing a plastic tube provided with an external sheath in accordance with another embodiment of the present disclosure.

The object of the present disclosure is a method for manufacturing a plastic tube provided with an external sheath. Specifically, a method for manufacturing a plastic tube suitable for molding a cuff thereon, includes: providing a plastic tube having an inner tube; covering the inner tube with an outer sheath; the outer sheath including at least a portion configured to be molded for producing the cuff; and injecting air intermittently or continuously between the inner tube and the sheath.

For a better understanding of the present disclosure the following embodiments are described, only in an exemplificative and not limitative way, with reference to the figures.

In FIG. 1a a tracheal tube, extruded and successively cut at the desired length, is indicated with 1. A superficial incision 2 has been cut out on the tracheal tube 1 to connect an inflation lumen (not shown) to the outside in relation to the cuff to be provided as described hereinafter.

FIG. 1b shows a metal core 3 around which the tracheal tube 1 is placed to form an assembly 4. In particular, the metal core 3 is hollow and comprises a connecting end 3a to be connected to a feeding line for compressed air L, and a truncated conical end 3b having some holes (not shown) for the outlet of the compressed air. As shown, the second end 3b having a truncated conical shape remains outside the tracheal tube 1.

FIG. 1c shows a second assembly 5 comprising an extruded and cooled sheath 6 inserted inside a metal tube 7. The position of the sheath 6 in the tube 7 is kept fixed by means of a clamp 8. In particular, the metal tube 7 has an inner diameter larger than the diameter of the sheath 6, so that said sheath 6, once inflated, can take on the size of the metal tube 7.

As shown in FIG. 1d, the assembly 5 is connected to the assembly 4 by bringing the truncated conical end 3b inside a first end of the sheath 6. The air injection through the truncated conical end 3b starts in this position, while at the same time the assembly 4 slides inside the assembly 5 obtaining a new assembly 9. During the sliding of the assembly 4 inside the assembly 5 the outcoming air inflates the sheath 6 and keeps it adherent to the metal tube 7 by simultaneously forming an air cushion around the tracheal tube 1. The thus formed air cushion allows the tracheal tube 1 to slide into the sheath 6, which, having an inner diameter smaller than the outer diameter of the tube and being made of an elastic material, stays adherent to the tracheal tube 1 as soon as the air cushion collapses.

FIG. 1e shows the splitting up of the assembly 9 once the sheath 6 has completely adhered to the tracheal tube 1. The splitting up occurs by releasing the clamp 8 and extracting from the metal tube 7 the tracheal tube 1 and the sheath 6 surrounding it. Once extracted, the portion of sheath 6 is cut in relation to the truncated conical end 3*b*, while inside the metal tube 7 a new portion of sheath 6 is placed for a new production cycle.

FIG. 1*f* shows the detachment of the metal core 3 from the tracheal tube 1, while the sheath 6 undergoes a finishing cut for adapting it to the size of the tracheal tube 1, thus obtaining the semifinished product of medical tube 10.

FIG. 1*g* shows the semifinished product 10 whereon an incision 11 is cut out for connecting in use the inflation lumen with a portion of the inflation tube it will be glued onto.

FIG. 1*h* shows a molding step wherein a portion of the semifinished product 10 comprising the incision 2 is inserted inside a die 12 for molding a cuff 13 and, therefore, for producing the medical tube 14. Die 12 is described and claimed in Italian Patent Application No. BO2009A000055 titled "Die for molding of a cuff on a plastic tube" filed on Feb. 5, 2009, the entire contents of which is hereby incorporated by reference.

With a reference to FIGS. 2*a*-2*d*, another embodiment of the method of the present disclosure will be described, which differs from the one relating to FIGS. 1*a*-1*h* because of its larger automation.

FIG. 2*a* shows a continuously extruded tracheal tube 21, cooled with air and on which a superficial incision 22 is cut out at a predefined distance for connecting the inflation lumen (not shown) to the cuff to be provided as described hereinafter. The tracheal tube 21 has such a stiffness that it does not need a metal core as was needed in the embodiments of FIG. 1.

Figure 2B:
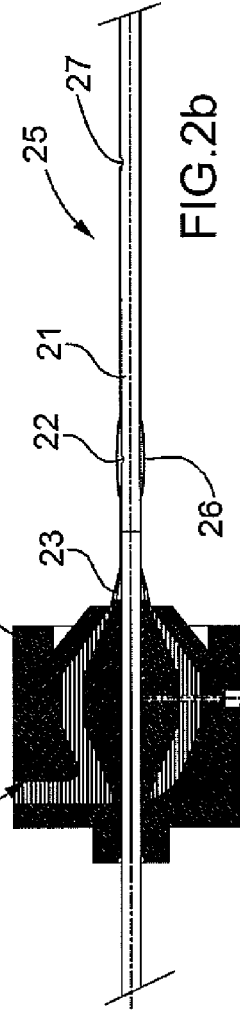

FIG. 2*b* shows a covering step of the tracheal tube 21 with a sheath 23. Once cooled and incised as previously described, the tracheal tube 21 is continuously inserted in a second extrusion head 24 by means of which the covering sheath 23 is produced by overextrusion. In particular, plastic material enters the extrusion head 24 through an inlet 24*b* and is overextruded around tube 21 forming the said sheath 23. During the overextrusion of the sheath 23, some air is injected at regular intervals between the tracheal tube 21 and the forming sheath 23. In particular, the air enters the extrusion head 24 through an inlet 24*a*, in use connected to a feeding line of compressed air, and is injected in relation to the superficial incisions 22 between the sheath 23 and the tracheal tube 21 so that some non-adhesion areas are formed around said incisions 22. It is thus obtained a semifinished medical tube 25 including a regularly distributed plurality of swellings 26 of the sheath 23 in the areas around the incisions 22. Afterwards, regularly distributed incisions 27 are cut out for connecting in use the inflation lumen to respective portions of the inflation tube they will be glued onto.

Figure 2C:
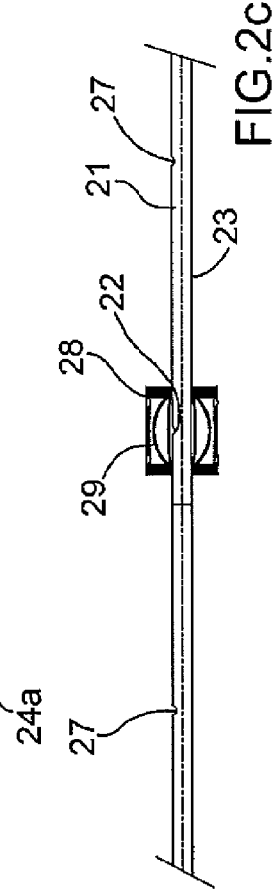

FIG. 2*c* shows the molding step, wherein a portion of semifinished medical tube 25 comprising a swelling 26 is inserted inside a die 28 for molding a cuff 29. As it is said about die 12, even die 28 is described and claimed in the Italian Patent Application titled "Die for molding of a cuff on a plastic tube", which is filed on the same day as this application in the name of Applicant and herewith incorporated by reference.

Figure 2D:
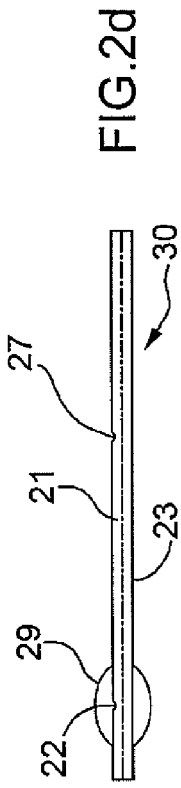

Finally, FIG. 2*d* shows a medical tube 30 obtained by cutting the semifinished medical tube 25 at predetermined points after the molding of the cuff 29.

As it clearly results from the aforesaid description, the method object of the present disclosure allows the production of a tracheal tube without using anti-adherent materials.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. Method for manufacturing a plastic tube having a cuff thereon, comprising the steps of:
    covering an inner tube with an outer sheath, said outer sheath including at least a portion configured to be molded for producing a cuff; and
    injecting air between said inner tube and said sheath, wherein the injecting step includes injecting air intermittently between said inner tube and said sheath.

2. Method according to claim 1, wherein said inner tube includes an inflation lumen.

3. Method according to claim 1, further comprising the step of:
    cutting out a plurality of first incisions on said inner tube for connecting the inflation lumen to the outside.

4. Method according to claim 3, wherein said injecting step comprises injecting air in relation to the first incisions so that the regularly distributed non-adhesion areas are formed around the first incisions.

5. Method according to claim 2, further comprising the step of:
    cutting out a second incision on said sheath and on said inner tube for connecting the inflation lumen to a portion of an inflation tube.

6. Method according to claim 1, wherein said covering step includes placing said inner tube around a metal hollow core, the metal hollow core including:
    a first end connected to a feeding line of compressed air and;
    a second end coming out from said inner tube, the second end having some holes for an outlet of the compressed air, said second end being first to be inserted in said sheath during the covering step.

7. Method according to claim 1, wherein said sheath has an inner diameter smaller than an outer diameter of the inner tube.

8. Method according to claim 3, further comprising the step of:
    molding a portion of the sheath, placed in relation to said plurality of first incisions on said inner tube, for producing a cuff.

9. Method according to claim 1, wherein said covering step includes an overextrusion of said sheath around said inner tube; said overextrusion being supported by said injecting step wherein some air is intermittently injected in order to produce regularly distributed non-adhesion areas between said sheath and said inner tube in relation to the plurality of first incisions.

10. Method according to claim 1, wherein said plastic tube is a medical tube.

11. Method according to claim 10, wherein the medical tube is one of a tracheal tube and a tracheostomy cannula.

* * * * *